United States Patent [19]
Taylot

[11] Patent Number: 5,571,973
[45] Date of Patent: Nov. 5, 1996

[54] MULTI-DIRECTIONAL PIEZORESISTIVE SHEAR AND NORMAL FORCE SENSORS FOR HOSPITAL MATTRESSES AND SEAT CUSHIONS

[76] Inventor: Geoffrey L. Taylot, 211 Oak Street, Winnipeg, Manitoba, Canada, R3M 3P7

[21] Appl. No.: 254,918

[22] Filed: Jun. 6, 1994

[51] Int. Cl.⁶ ........................................ G01L 3/00
[52] U.S. Cl. .................. 73/862.046; 73/DIG. 4
[58] Field of Search ................ 73/862.041–862.043, 73/862.046, 862.625–862.627, 862.637, 862.68, 841, 727, DIG. 4; 128/774, 779

[56] References Cited

U.S. PATENT DOCUMENTS

| | | | |
|---|---|---|---|
| 4,644,801 | 2/1987 | Kustanovich | 73/862.046 X |
| 4,703,663 | 11/1987 | Oppermann | 73/862.68 |
| 4,802,371 | 2/1989 | Calderara et al. | 73/862.043 |
| 4,827,763 | 5/1989 | Bourland et al. | 73/862.046 X |
| 4,934,197 | 6/1990 | Nitsche | 73/862.68 X |
| 5,010,774 | 4/1991 | Kikuo et al. | 73/862.046 |
| 5,054,323 | 10/1991 | Hubbard, Jr. et al. | 73/DIG. 4 X |
| 5,060,527 | 10/1991 | Burgess | 73/862.046 X |
| 5,083,467 | 1/1992 | Tabota | 73/862.046 |
| 5,209,126 | 5/1993 | Grahn | 73/862.046 |
| 5,341,687 | 8/1994 | Stan | 73/862.046 |

Primary Examiner—Richard Chilcot
Assistant Examiner—Elizabeth L. Dougherty
Attorney, Agent, or Firm—William L. Chapin

[57] ABSTRACT

Thin, planar sensors for measuring forces exerted by mattresses or chair pads on a patient's body include a central conductive elastomeric pad movable in a horizontal plane into more or less intimate contact with flexible peripheral conductors adjacent the central pad, thus varying electrical conductivity between the central pad and peripheral conductors by a surface piezoresistive effect proportional to the magnitude and direction of horizontal shear forces exerted on the pad. The preferred embodiment comprises a matrix area array of thin, square central conductive elastomeric pads, each surrounded by four square peripheral conductive elastomeric pads forming a close pack tiling arrangement that utilizes inner peripheral conductors in the array to function as one of the peripheral conductors for two or three nearest-neighbor sensors. In one embodiment of the invention, a sensor having a thin, flat layer formed of a non-conductive elastomeric polymer matrix filled with electrically conductive particles is sensitive to pressure or normal forces exerted on the sensor, such forces reducing the volume of the layer and therefore its electrical resistance, by a bulk on volume piezoresistive effect.

36 Claims, 13 Drawing Sheets

MULTI-DIRECTIONAL PIEZORESISTIVE SHEAR AND NORMAL FORCE SENSORS FOR HOSPITAL MATTRESSES AND SEAT CUSHIONS

BACKGROUND OF THE INVENTION

A. Field of the Invention

The present invention relates to apparatus and equipment used in conjunction with patient care in hospitals, convalescent homes and the like. More particularly, the invention relates to sensors for measuring shear and normal forces exerted on body tissues of a seated or recumbent patient.

B. Description of Background Art

Patients in hospitals, nursing homes, and the like, who are required to sit or lie for long periods are thereby subjected to the problem of formation of decubitus ulcers, commonly referred to as bedsores. These result from normal (perpendicular) forces or pressures exerted on areas of the body by a bed or chair, and from tangential or shear forces exerted by different portions of a mattress or cushion supporting a patient. If such forces are exerted on the same parts of a patient's body for sufficiently long periods, body tissues can be broken down, resulting in the formation of painful and sometimes dangerous decubitus ulcers. The deterioration process may be accelerated by such things as poor health, moisture, especially if relatively acidic or alkaline, i.e., having a pH deviating substantially from the pH 7 of pure water, and high temperature. If the conditions causing decubitus ulcers, including high shear forces, are sufficiently great, nasty sores can be caused, which can lead to a lengthy, expensive recovery, medical complications, and even death.

A wide variety of instruments are available for measuring pH, humidity and temperature. Also, the present inventor has developed and is marketing a normal force measurement device for use in monitoring pressures exerted by cushions and mattresses on a patient's body. This device is the Force Sensing Array and is available from Vistamed Corp., P.O. Box 23058, 1315 Pembina Highway, Winnipeg, Manitoba, Canada R3T 5S3. However, the present inventor is unaware of the existence of any devices adapted to measure shear forces exerted in the support of a patient's body by a mattress or cushion, either separately or in combination with normal forces. The present invention was conceived of to fill a perceived need for sensors capable of measuring such forces.

OBJECTS OF THE INVENTION

An object of the present invention is to provide a shear sensor or transducer for measuring non-collinear reaction forces exerted on parts of a patient's body resting on a cushion or mattress.

Another object of the invention is to provide a thin, flexible shear sensor adapted to producing electrical signals that permit remote monitoring of tangential shear forces exerted by a mattress or cushion on portions of a patient's body.

Another object of the invention is to provide a shear sensor adapted to produce a plurality of electrical signals that collectively indicate magnitude and direction of shears exerted on the sensor.

Another object of the invention is to provide a shear sensor adapted to produce electrical signals that indicate unambiguously the action direction of a shear applied to the sensor.

Another object of the invention is to provide an area array of shear sensors, each adapted to produce a plurality of individual electrical signals indicative of the magnitude and direction of shears at various positions over the area of the array.

Another object of the invention is to provide a multi-directional shear sensor apparatus adapted to produce a digital map of the magnitude and direction of shears exerted over an area in conformal contact with a shear sensor array.

Another object of the invention is to provide a shear sensor array enclosed in a thin, flexible waterproof enclosure that may be placed beneath a patient, under a mattress pad or the like, without causing discomfort to the patient.

Another object of the invention is to provide a thin, flexible normal force sensor for monitoring pressure exerted by a mattress or cushion on a patient's body.

Another object of the invention is to provide a thin, flexible waterproof force sensor array capable of measuring both shear forces and normal forces over an extended area, the array being positionable beneath a patient without causing discomfort to the patient.

Various other objects and advantages of the present invention, and its most novel features, will become apparent to those skilled in the art by perusing the accompanying specification, drawings and claims.

It is to be understood that although the invention disclosed herein is fully capable of achieving the objects and providing the advantages described, the characteristics of the invention described herein are merely illustrative of the preferred embodiments. Accordingly, I do not intend that the scope of my exclusive rights and privileges in the invention be limited to details of the embodiments described. I do intend that equivalents, adaptations and modifications of the invention reasonably inferable from the description contained herein be included within the scope of the invention as defined by the appended claims.

SUMMARY OF THE INVENTION

Briefly stated, the present invention comprehends novel sensors for measuring forces exerted on a patient's body by mattresses or cushions supporting the patient.

A shear force sensor according to the present invention includes a central thin, flexible electrically conductive, elastomeric pad surrounded by a plurality of elastomeric, peripheral conductors in resilient peripheral contact with sidewalls of the central pad. Horizontal movement of the central pad relative to the peripheral conductors causes some peripheral conductors to be urged into more intimate contact with sidewalls at the central pad, and other peripheral conductors to be in less intimate contact with the pad, thereby causing a change in electrical resistance between the central conductive pad and the peripheral conductors, proportional to the size of contact area between the resiliently deformable central pad and peripheral conductors and therefore to shear forces exerted on the central pad. This variation of electrical resistivity as a function of contacting force is referred to herein as surface piezoresistivity.

In one embodiment of a shear sensor according to the present invention, the central conductive elastomeric pad has a triangular plan view shape, and is of thin, uniform cross-section. In this embodiment, the peripheral conductors are wire-like, elongated, conductive elastomeric cylinders or "wires," a separate cylinder being in contact with each of the sidewalls of the central conductive pad. In the preferred embodiment, the conductive wires and pads are fastened to a thin, flexible rubber substrate sheet, and encapsulated by a thin, flexible rubber cover sheet. Also in the preferred embodiment, the lower surface of the central conductive pad has adhered thereto a thin, slippery sheet made of a flexible polymer material, which is slidable on a similar sheet of material adhered to the upper surface of the substrate sheet.

In the preferred embodiment of the present invention, a plurality of novel shear sensors is arranged into a rectangular matrix or area array, allowing measurement of shear forces at a plurality of matrix locations.

In a second embodiment of a shear force sensor according to the present invention, the walls of a thin, rectangularly-shaped conductive elastomeric pad are resiliently contacted by four rectangularly-shaped peripheral conductive elastomeric pads.

In a modification of either the triangular or rectangular shear sensors according to the present invention, normal force sensing means are incorporated into one or more of the shear sensors in an array. In this modification, a layer of partially conductive, resiliently compressible ink is applied to the surface of the central conductive pad of a shear sensor. The ink contains a conductive filler such as finally divided conductive carbon particles in a matrix of a non-conducting elastomeric polymer. Pressure on the ink decreases the volume of non-conductive matrix relative to conductive filler, thereby decreasing the volume electrical resistivity. This dependence of resistivity on pressure is referred to herein as bulk or volume piezoresistivity. A flexible conductive fabric sheet overlying the conductive ink forms one terminal of a pressure sensitive piezoresistive sensor element, with the conductive central pad forming the other terminal of the element. Thus constructed, the sensor provides a variable electrical resistance proportional to normal forces or pressures perpendicularly oriented with respect to the pad, and simultaneously provides variable electrical resistances proportional to the magnitude and direction of horizontally directed shear forces exerted on the pad.

DETAILED DESCRIPTION OF THE PREFERRED EMBODIMENTS

FIGS. 1 through 21 show novel multi-directional shear and normal force sensors for hospital beds according to the present invention.

Figure 1:
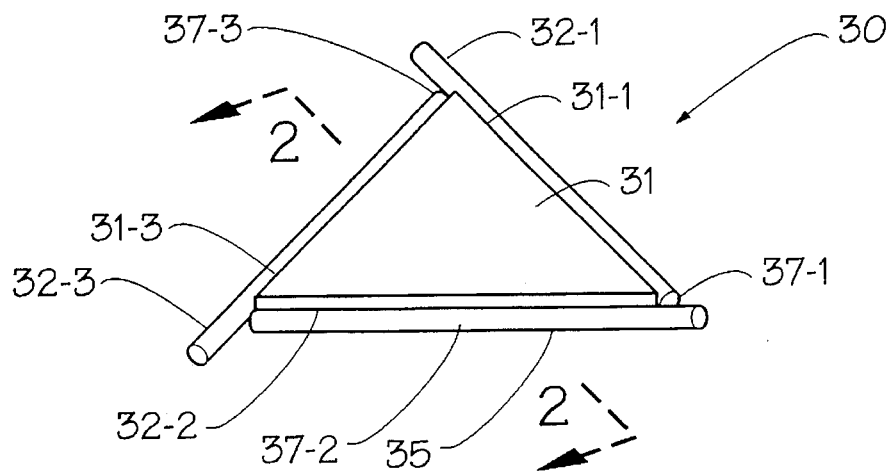
FIG. 1 is an upper perspective view of a first, triangular embodiment of a shear sensor according to the present invention, showing an upper cover sheet thereof peeled back to reveal details of the sensor.
Figure 2:
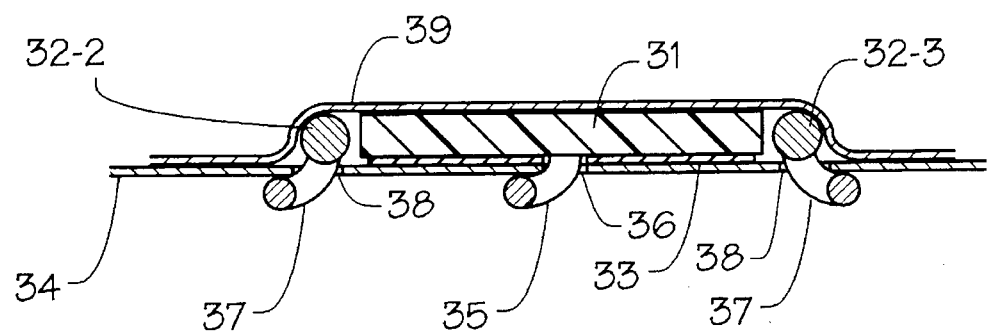
FIG. 2 is a transverse sectional view of the sensor of FIG. 1, taken along line 2—2.

Referring first to FIGS. 1 and 2, a basic embodiment of a shear sensor according to the present invention is shown. As shown in FIGS. 1 and 2, shear sensor 30 includes a central triangular-shaped electrically conductive pad 31 of thin, uniform cross section. Central conductive pad 31 is preferably made of a conductive elastomeric polymer. One suitable material for pad 31 is a conductive synthetic rubber sheet having a thickness of about 0.025 inch thick, manufactured by Stockwell Rubber Company, 4749 Talbut Street, Philadelphia, Pa. 19139, Part No. SE65Con. This material has a volume resistance of 5 ohm/cm. Preferably, the conductivity of pad 31 is tailored to the range of shear forces which it is desired to measure with sensor 30. For that reason, it has been found preferable to custom-compound molding material for pad 31 by mixing carbon black or finely powdered graphite with room-temperature vulcanizing silicone rubber, such as Dow RTV 732, manufactured by the Dow Corning Canada Corporation, Mississauga, Ontario Canada LSN 2M1.

The concentration of carbon black or powdered graphite in liquid or unpolymerized silicone rubber typically must be greater than 50% by volume. The mixture is milled together and checked for continuity. Since the fill ratio is very critical, it is desirable to continuously measure conductivity of the mixture while adding conductive filler until the volume resistivity of the mixture drops below about 10K ohm-cm. The mix is then spread or molded to the desired shape, and allowed to air-cure at room temperature.

Sensor 30 includes a plurality of peripheral, electrically isolated resilient conductors 32 that conductively contact the sidewalls of central conductive pad 31. As shown in FIGS. 1 and 2, peripheral conductors 32 have the shape of small diameter, elongated cylinders, and may therefore be referred to as "wires." A suitable material for wires 32 is a silicone rubber cylinder having a silver-flake impregnated silicon rubber exterior layer vulcanized to the cylinder. Such cylinders are marketed as Part No. 7072 by Vanguard Products Corporation, 144 Old Brookfield Road, Danbury, Conn.

Figure 3:
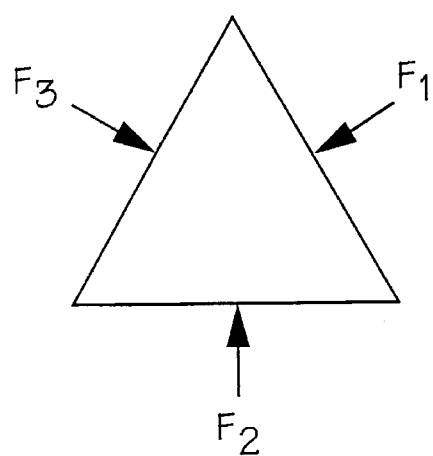
FIG. 3 is a diagrammatic upper plan view of a sensor of the type shown in FIG. 1, defining the directions of horizontal forces applied to sides of the sensor.
Figure 4:
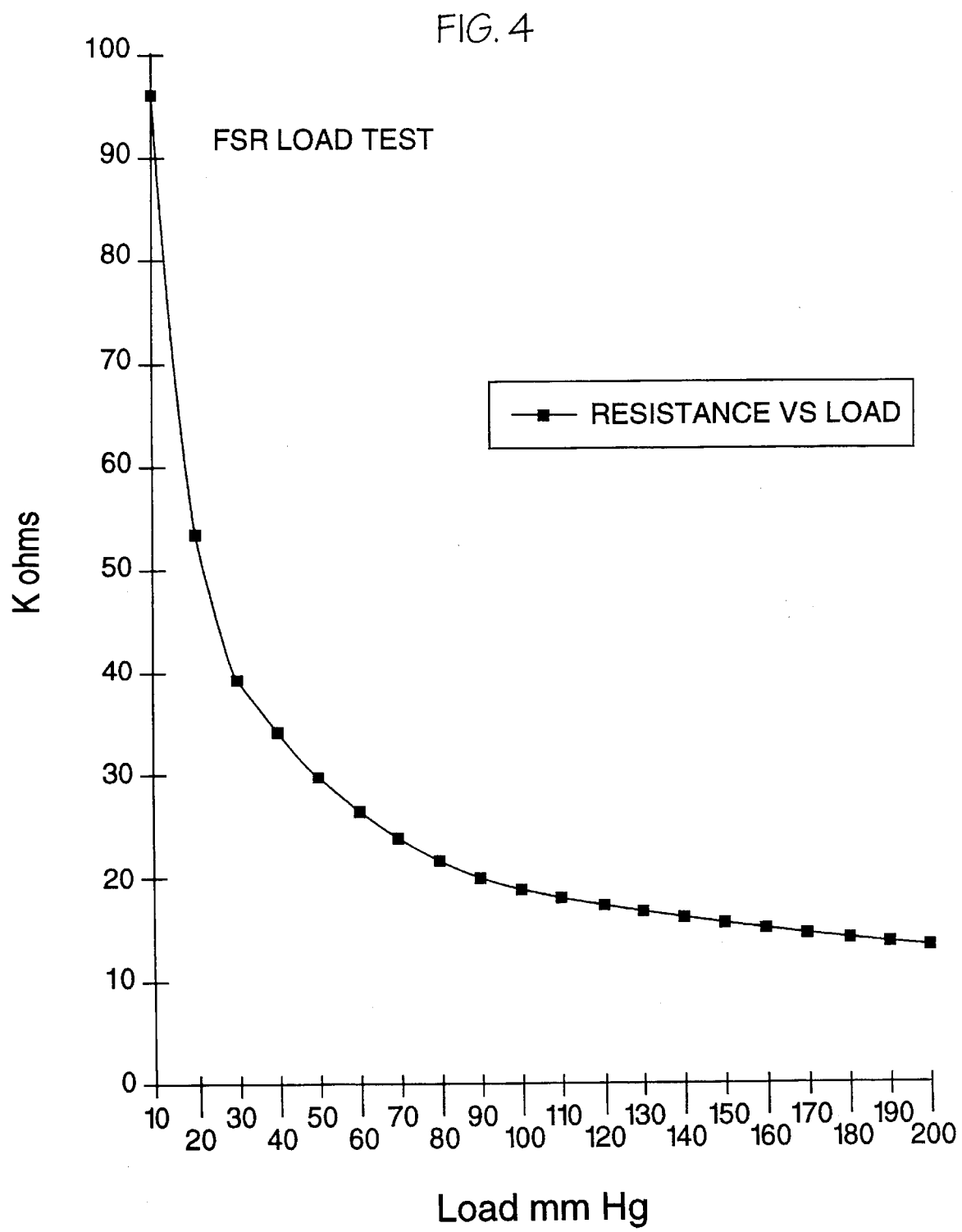
FIG. 4 is a graph of resistance versus shear force for the sensor of FIG. 1.

As shown in FIG. 3 and which will be described in detail later, forces in a horizontal plane exerted on peripheral conductors 32 cause those conductors to contact adjacent sidewalls of central conductive pad 31 more or less tightly, decreasing or increasing contact area and thereby decreasing or increasing the electrical resistance between the peripheral conductors and central conductive pad. FIG. 4 illustrates a typical variation of the resistance of sensor 30 as a function of force urging a peripheral conductor 32 into more intimate contact with central conductive pad 31, a property which may be referred to as surface piezoresistivity.

Referring again to FIGS. 1 and 2, the manner of making electrical connections to central conductive pad 31 and peripheral conductors 32 will now be described. As shown in FIG. 1 and 2, an electrode 33 is attached to the lower surface of central conductive pad 31. A suitable material for electrode 33 is a conductive fabric, marketed under the name Flectron nickel/copper polyester taffeta by Monsanto, The Chemical Group, 800 N. Lindberg, St. Louis, Mo. This material has a thickness of 3.8 to 4 mils, is flexible and drapable, and has a surface resistivity of less than 0.05 ohms per square.

Electrode 33 is cut to approximately the same plan view shape as central conductive pad 31, but somewhat smaller, so as to prevent direct contact between the electrode and peripheral conductors 32. Electrode 33 is attached to the lower surface of central conductive pad 31 by any suitable means, but preferably by strips of thin tape coated on both sides with pressure sensitive adhesive and referred to as "double stick" tape. These strips (not shown) are sandwiched between the electrode and the pad.

In the embodiment of sensor 30 shown in FIGS. 1 and 2, central conductive pad 31 is fastened to a lower thin, moisture impervious substrate sheet 34, preferably a latex rubber sheet having a thickness of about 0.004 inch. In one version of the embodiment of sensor 30 shown in FIGS. 1 and 2 and tested by the present inventor, central conductive pad 31 was adhered to latex substrate sheet 34 by strips of double stick tape sandwiched between the lower surface of central electrode 33 and the upper surface of the substrate sheet. Electrical contact was made to central electrode 33 by means of a small diameter wire 35 protruding through a hole 36. The upper end of wire 35 is preferably attached to central electrode 33 by a conductive glue such as RTV 60C conductive adhesive, manufactured by Stockwell Rubber Company, 4749 Talbut Street, Philadelphia, Pa. 19136.

As shown in FIG. 2, electrical connections to peripheral conductors 32 are made by means of wires 37 protruding through holes 38 through latex substrate sheet 34, one such hole being adjacent an end of each of the three peripheral conductors. Preferably, however, each silver coated silicone wire used to fabricate peripheral conductors 32 is made longer at one end, and pushed through a hole 38, the downwardly protruding portion of the wire comprising the interconnecting conductor to the peripheral conductor.

Peripheral conductors 32 are fastened to the upper surface of latex substrate sheet 34 by RTV 60C conductive adhesive. Sensor 30 is formed into a sealed, moisture impervious unit by stretching a thin, latex cover sheet 39 over central conductive pad 31 and peripheral conductors 32, and sealing the cover sheet to substrate sheet 34 by a contact cement such as Elmer's Safe-T contact cement, latex formula, manufactured by Borden, LTD., Willow Drive, Ontario, Canada. Although sensors 30 may be constructed in any desired size, I have found that a suitable shape and size for central conductive pad 31 is an equilateral triangle ½ inch on a side. In the preferred embodiment, the upper surface of central conducting pad protrudes about 0.030 inch above the upper surface of peripheral conductors 32. Thus, in this embodiment, shear forces on the central conducting pad would tend to move it with respect to the peripheral conductors. In a first variation of this arrangement, the height of central conducting pad is made less than that of the peripheral conductors. In this variation, shear forces on the peripheral conductors would tend to move them with respect to the central conducting pad. In a second variation of the basic arrangement of sensor 30, the central conducting pad and peripheral conductors may be of the same height. With this arrangement, the upper surfaces of the central conducting pad and peripheral conductors preferably have different coefficients of friction. This difference promotes movement of the conductor having a higher coefficient of friction relative to the conductors having a smoother upper surface, in response to tangential forces exerted in the upper surface of the sensor.

FIG. 3 defines the directions of horizontal or shear forces that sensor 30 is sensitive to. The force components along two orthogonal directions in the plane of sensor 30, taken as the X-Y plane in FIG. 3 is:

$$F_x=(F_3-F_1) \sin 60°=(F_3-F_1) (0.866)$$

$$F_y=F_2-(F_1+F_3) \cos 60°=F_2-(F_1+F_3) (0.5)$$

Were $F_x$ is the X component of shear, $F_y$ is the Y component of shear and $F_1$, $F_2$, and $F_3$ are the perpendicular horizontal forces exerted on peripheral conductors 32-1, 32-2 and 33-3 by side walls 31-1, 31-2, and 32-3, respectively, of central conductive pad.

Thus, the magnitude and direction of shear forces in any direction in the X-Y plane can be resolved by measuring the forces $F_1$, $F_2$ and $F_3$ by monitoring the resistance between central conductive pad 31 and the three peripheral conductors 32 shown in FIGS. 1 and 2.

Figure 5:
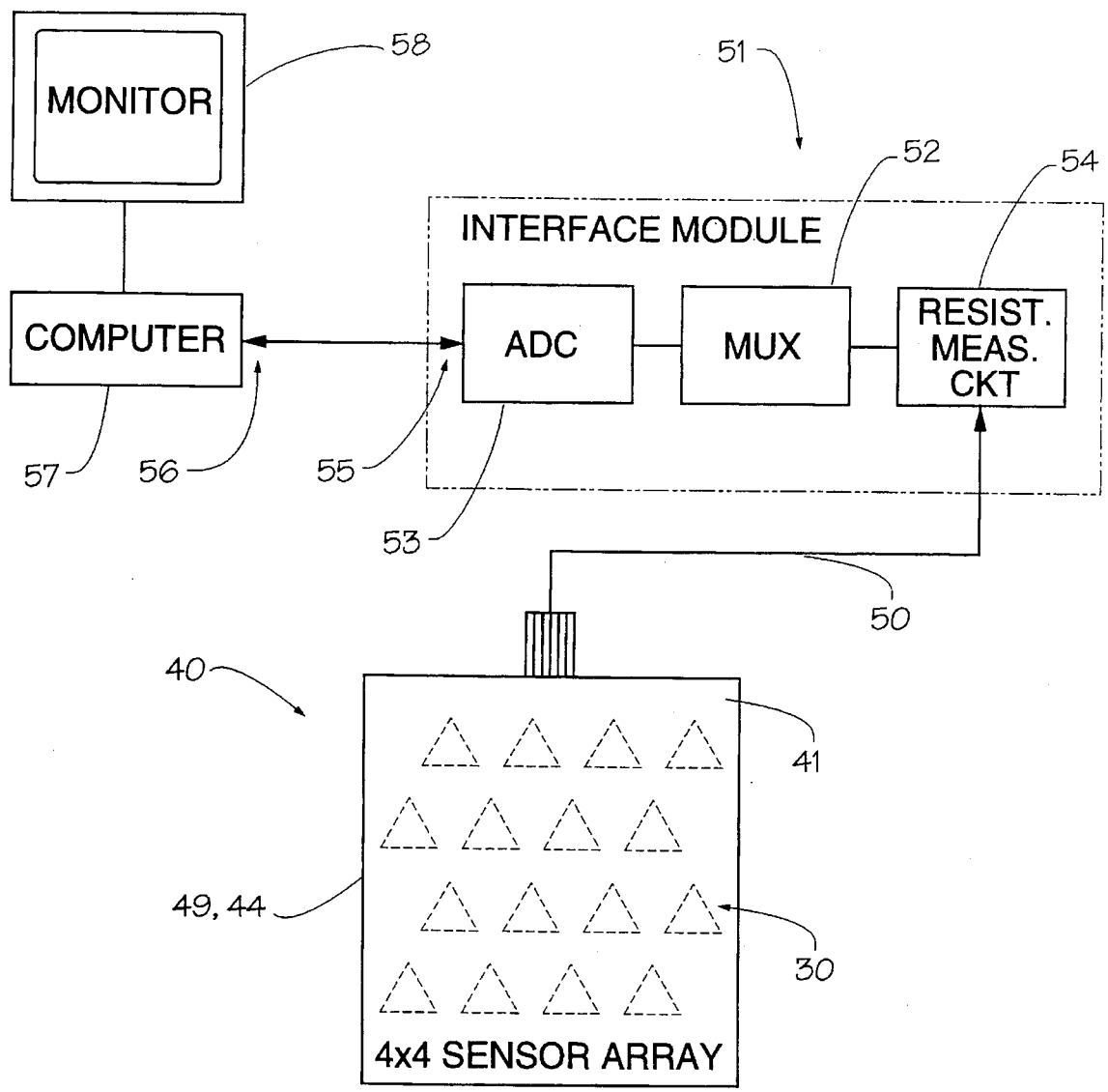
FIG. 5 is a partially diagrammatic block diagram of a rectangular array of sensors of the type shown in FIG. 1, showing the array interconnected with processing and display circuitry.

FIG. 5 is a partially diagrammatic view of a planar area array 40 of sensors 30 of the type shown in FIGS. 1 and 2 and described above, showing the array connected to signal processing and display circuitry. As shown in FIG. 5, sensor array 40 includes a 4×4 rectangular matrix of shear sensors 30, for a total of 16 sensors. Although both the sensor size and spacing between sensors could be any desired values, a typical sensor array 40 may consist of sensors 30 having ½ inch long sides, and spaced ¾ inch apart, resulting in a square array approximately 4-½ inches on a side.

Sensor array 40 may be constructed by adhering conductively encapsulated sensors 30 to a flexible base plate and then enclosing the array by sealing a flexible cover sheet to the base plate. Preferably however, sensor array 40 is constructed by fastening a plurality of spaced apart central conductive pads 31 and their associated peripheral conductors 31 to a single common rectangularly shaped, flexible, water impervious, substrate sheet 44, and enclosing the array of sensors 30 so constructed by a single rectangularly shaped, flexible, water impervious cover sheet 49, sealed at its peripheral edges to the substrate sheet.

As shown in FIG. 1, and referring to FIGS. 3 and 4, using sensor 30 to measure both the magnitude and direction of shear forces exerted in any direction in the plane of the sensor requires the measurement of three separate electrical resistances, namely, the resistances between the central conductive pad 31 and each of three peripheral conductors 32. Accordingly, 4 electrical conductors must be brought out from each sensor 30 to permit measurement of the three resistances indicative of shear forces exerted on the sensor. For the array 40 of 16 sensors 30 shown in FIG. 5, a single common conductor may connect to each central conductor pad, so that the total number of conductors required in sensor array interface cable 50 is one plus 16×3=49. In the preferred embodiment, a flat, multi-conductor ribbon cable is used for interface cable 50.

As shown in FIG. 5, interface cable 50 is connected at one end thereof to sensor array 40, and at the other end thereof to an interface module 51 containing means for applying an electrical sampling signal between the central conductive pad 31 and each of the three peripheral conductors 32 of a selected sensor 30, to measure three resistance values of the sensor. Resistance is measured by applying a fixed voltage across a sensor resistance element, and measuring the resulting current, or applying a fixed current, and measuring the voltage drop. Although a d.c. sampling signal may be used for measuring resistances of sensors 30, preferably, an a.c. signal is used, to avoid polarizing effects on the sensors.

To minimize the number of signal leads used to monitor resistance values of sensor array 40, interface module 51 preferably contains a multiplexer 52, which sequentially outputs a sequence of 48 signals, each signal being representative of one of the three discrete resistance values for a particular one of the 16 sensors. Also in the preferred embodiment, an analog-to-digital converter (ADC) 53 is connected between an analog resistance measuring circuit 54 and multiplexer 52, which is then of the digital variety, outputs a serial digital data signal on an RS232 port 55. In the preferred embodiment, RS232 port 55 of interface module 51 is connected to serial data port 56 of a computer 57.

Computer 57 is used to control interface module 51, directing the sequence of addressing sensors 30 in array 40. Computer 57 also performs signal processing functions, using predetermined scaling factors to convert the resistance values of sensors 30 to digital values representing shear forces exerted on the sensors. In the preferred embodiment, digital numbers representing the magnitudes and directions of shear forces on each of the 16 sensors 30 in array 40 are utilized to produce an area map of those forces, which is displayed on a monitor 58 and stored in digital memory if desired.

Figure 6:
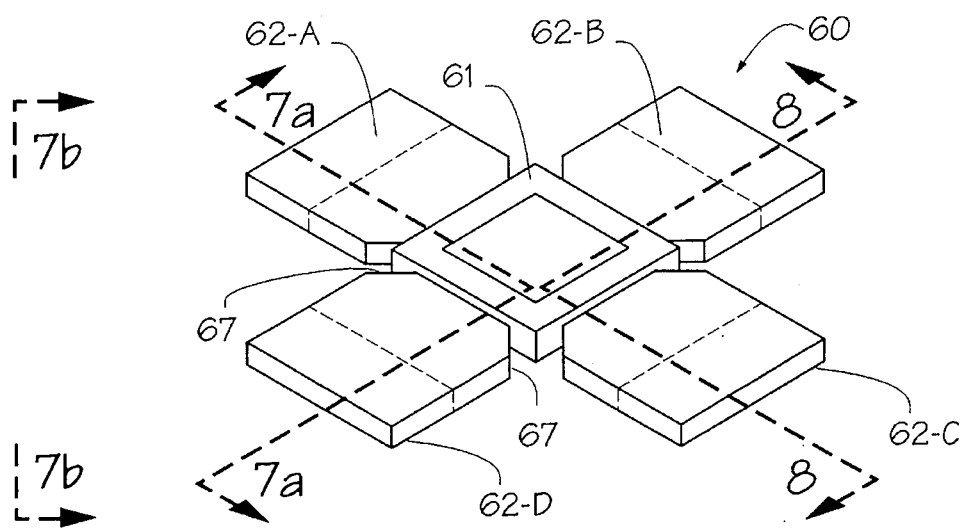
FIG. 6 is an upper perspective view of a second, rectangular embodiment of a shear force sensor according to the present invention, showing upper a fragmentary cover sheet thereof peeled back

FIG. 6 shows a second embodiment of a shear sensor according to the present invention, which is a modification of shear sensor 30 shown in FIG. 1. As shown in FIG. 6, modified shear sensor 60 includes a central rectangular, preferably square, shaped electrically conductive pad 61 having a thin, uniform cross-section. Central conductive pad 61 is made of a conductive elastomeric polymer having characteristics described in detail above in conjunction with the discussion of the basic embodiment of a shear sensor according to the present invention. Sensor 60 includes a plurality of peripheral, electrically isolated resilient conductors 62 that resiliently and conductively contact the sidewalls of central conductive pad 61. As shown in FIG. 6, peripheral conductors 62 preferably have the shape of thin pads having a square plan view of approximately the same size as that of central conductive pad 61. For a single sensor of the type shown in FIG. 6, peripheral conductors 62 could be thin, elongated rectangular strips, the outer lateral edges of which are indicated by dashed lines. However, as shown in FIG. 6 for constructing a rectangular matrix array of sensors 60, it is desirable to have 4 peripheral conductive pads 62-A, 62-B, 62-C and 62-D, each of the same size and shape as central conductive pad 61, for reasons that will become apparent in the ensuing discussion of such a matrix array.

Referring still to FIG. 6, it may be seen that the inner straight edge wall of each peripheral conductor 62 contacting an outer edge wall of central conductive pad 61 is made shorter than the contacting central pad edge wall, by means of a pair of straight, symmetrical bevel cuts 67 extending outwards from the inner edge wall to the adjacent side edge wall of the peripheral conductor. This arrangement prevents physical and conductive contact between adjacent peripheral conductor pads 62, such as between pads 62-C and 62-C or 62-D in FIG. 6. Such contacts would result in an electrical short circuit.

Figure 7A:
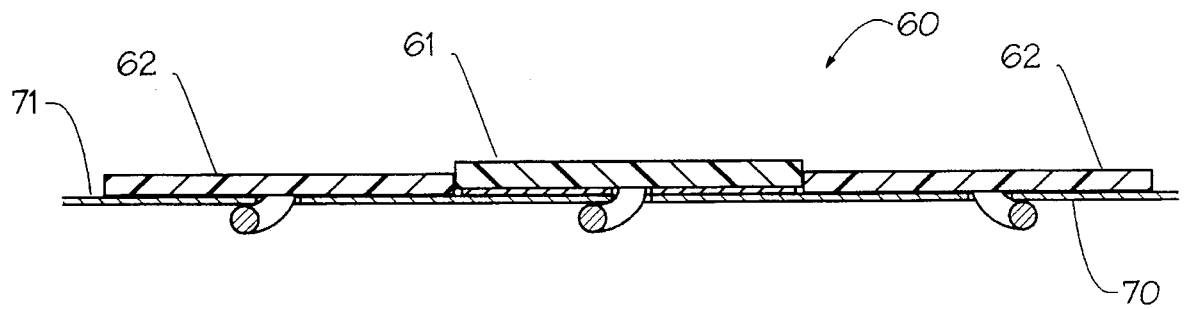
FIG. 7A is an oblique sectional view of the sensor of FIG. 6, taken along line 7—7 and showing in addition a first embodiment of electrical connection means to the sensor.

As so far described, square shear sensor 60 could be constructed similarly to triangular shear sensor 30 described above. Thus, as shown in FIG. 7A separate electrical connections could be made to central square conductive pad 61 and the four square peripheral conductive pads 62 exactly as described above and shown in FIG. 2. Preferably, however, construction details of sensor 60 are modified, as shown in FIGS. 7B and 8.

Figure 7B:
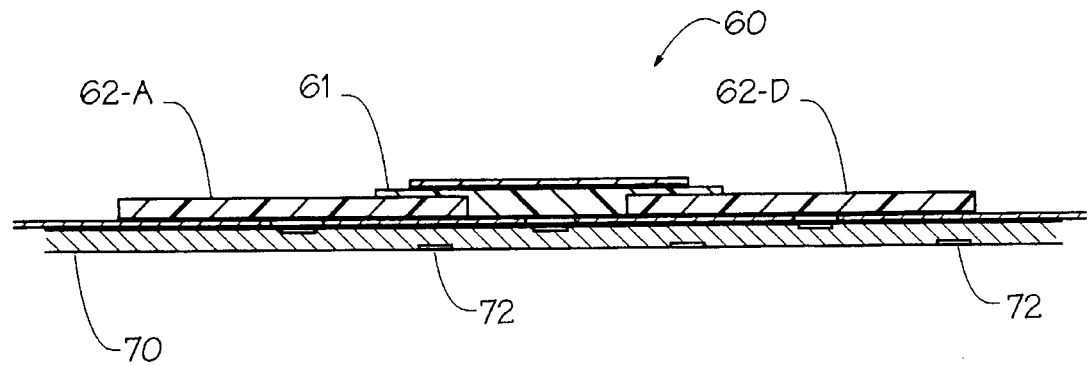
FIG. 7B is an oblique sectional view of the sensor of FIG. 6, taken along line 7—7 and showing in addition a second embodiment of electrical connection means to the sensor.
Figure 8:
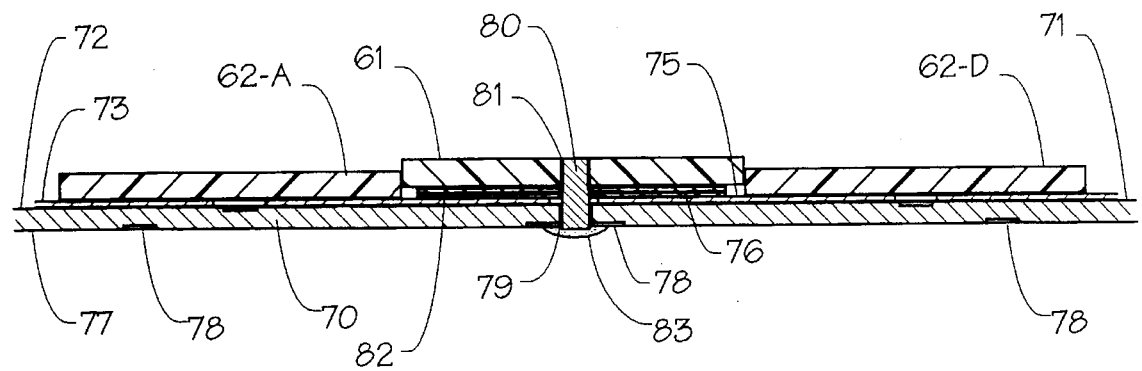
FIG. 8 is a zig-zag sectional view of the sensor of FIG. 6, taken along line 8—8 and showing additional elements of the second embodiment of electrical connection means to the sensor of FIG. 7B.
Figure 10:
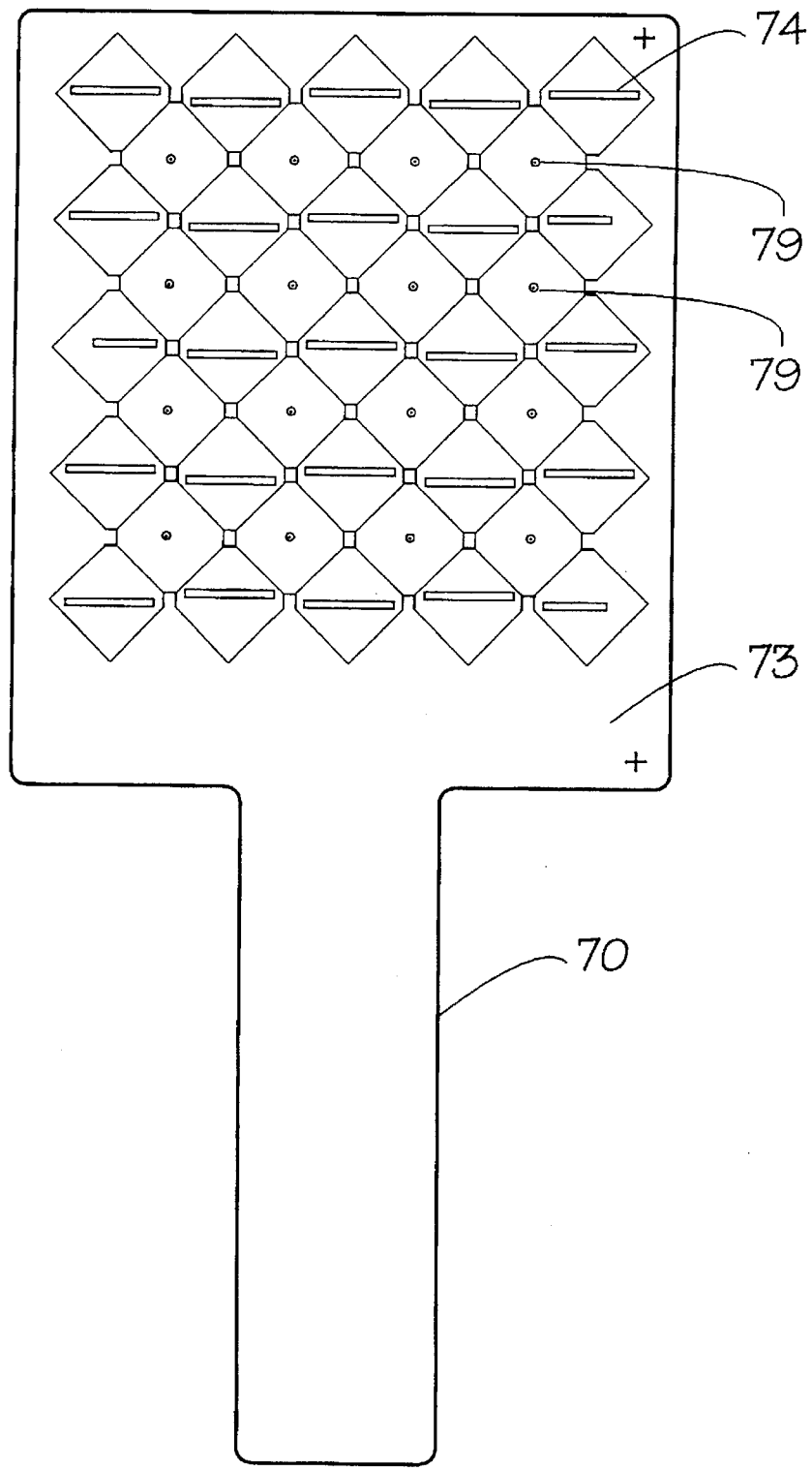
FIG. 10 is an upper plan view of a flexible printed circuit comprising part of the sensor array of FIG. 9.
Figure 11:
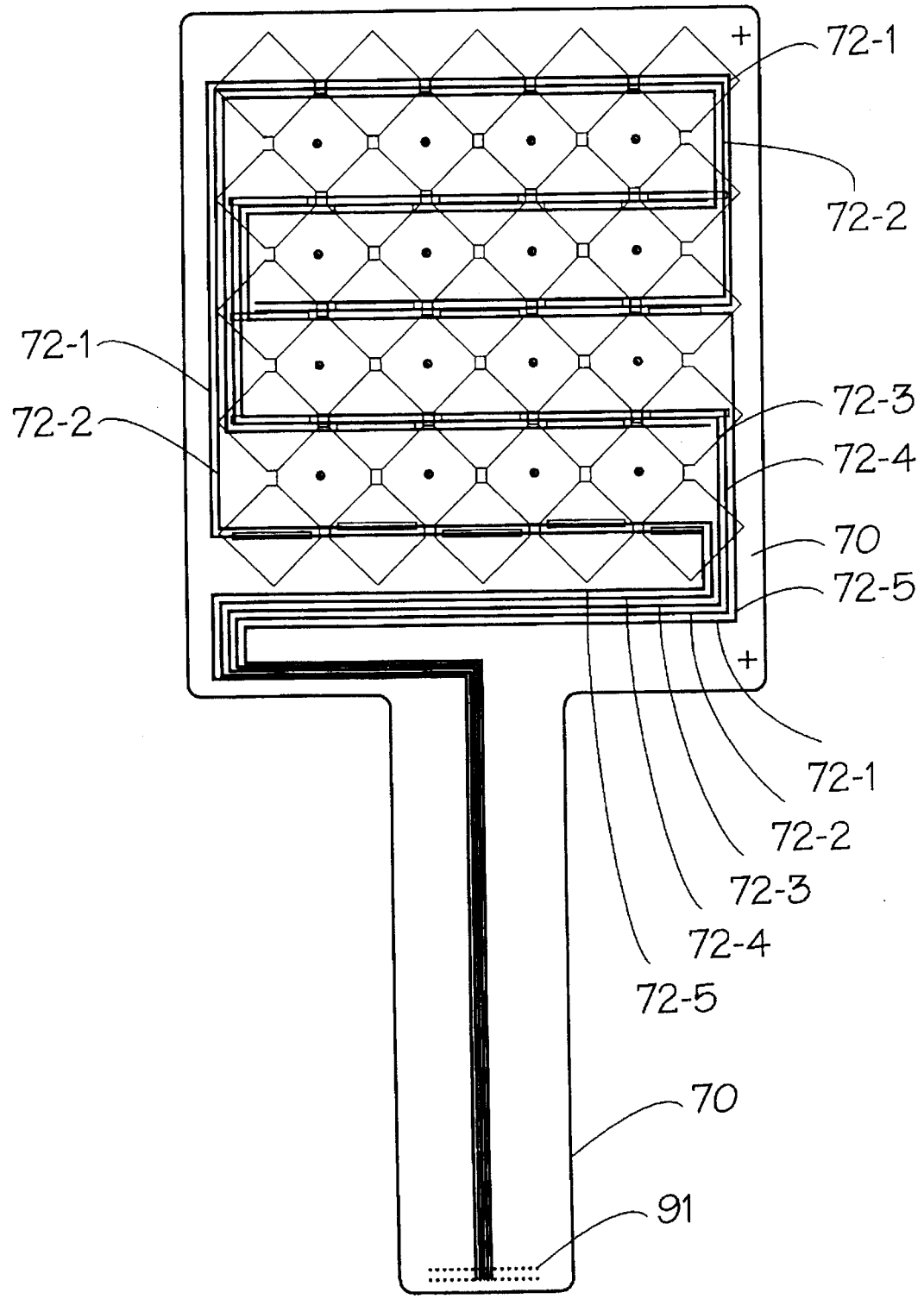
FIG. 11 is a fragmentary, partly sectional upper view of the printed circuit of FIG. 10.

Referring now to FIGS. 7B and 8, sensor 60 is shown mounted on a flexible printed circuit substrate 70, rather than on a latex sheet 34 of sensor 30 shown in FIG. 2. Preferably, substrate 70 is made of a thin, flexible polymer such as KAPTON™ brand flexible circuit board distributed by Norplex Oak, P.O. 910639, Dallas, Tex. 75398-0639. Flexible printed circuit substrate 70 has conductive traces on both its upper and lower surfaces which are used to conductively contact central conductive pad 61 and peripheral conductive pads 62. Thus, as shown in FIGS. 6, 10 and 11, flexible printed circuit 70 has on its upper surface 71 a plurality of elongated conductive metallic traces 72 overlain by a thin insulating cover sheet 73. As shown in FIG. 10, thin insulating cover sheet 73 has a plurality of elongated rectangular openings 74 vertically aligned and in electrically conductive contact with the undersides of peripheral conductive pads 62. As may be seen best by referring to FIG. 8, in the preferred embodiment, a thin sheet 75 of a highly lubricous polymer such as polyethylene or TEFLON™ is adhered to the underside of central conductive pad 61. The purpose of slippery lower sheet 75 is to permit central conductive pad 61 to slide freely relative to peripheral conductive pads 62, in a plane parallel to substrate 70, thus increasing the responsivity or sensitivity of sensor 60 to horizontally directed shear forces. With this arrangement, central conductive pad 61 is held in place on printed circuit 70 solely by a flexible connecting wire, as is described below. Optionally, an additional slippery sheet 76 may be adhered to the upper surface of substrate 70, one under each central pad 61.

Figure 12:
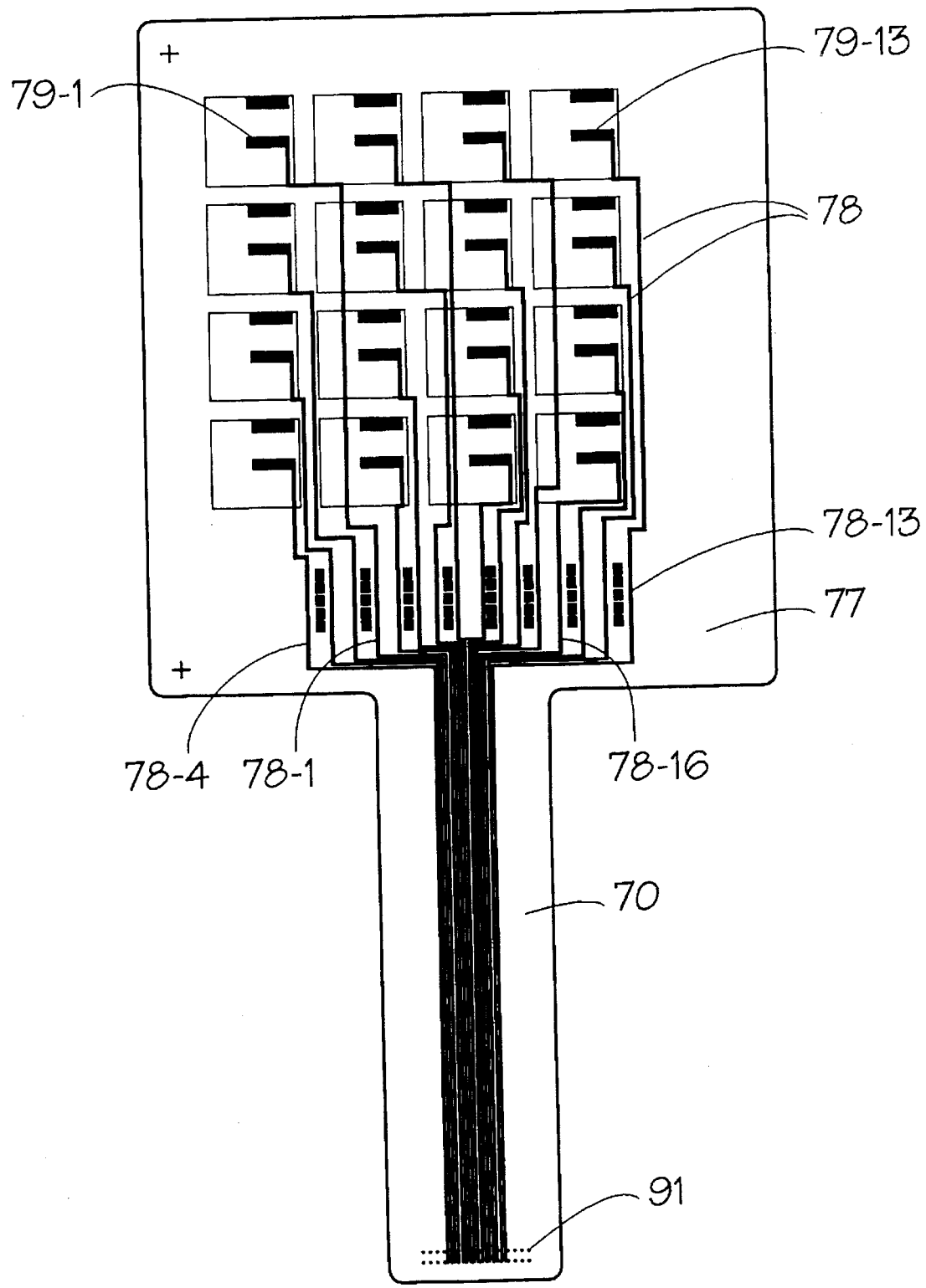
FIG. 12 is a lower plan view of the printed circuit of FIG. 10.

The manner of making electrical connection to the central conductive pad 61 of sensor 60 may be best understood by referring to FIGS. 8 and 12. As shown in those figures, printed circuit substrate 70 has on the lower surface 77 thereof a plurality of conductive metal traces 78. One such trace 78 terminates in a location underlying the center of central conductive pad 61 of each sensor 60. At this location, a hole is formed through printed circuit substrate 70, and is plated with metal to form a plated-through hole or via 79 in electrically conductive contact with trace 78. Via 79 receives a flexible, conductive silver coated rubber wire 80, of the type previously described. Wire 80 is resiliently received in a centrally located bore 81 extending upwards from the lower face 82 of central conductive pad 61. Bore 81 is of slightly smaller diameter than elastomeric wire 80, and therefore tightly grips and makes good electrical contact with the wire. Wire 80 is secured to printed circuit substrate 70 by a drop 83 of electrically conductive glue such as RTV 60C. FIG. 9 through 15 illustrate a 4×4 square matrix array of square detectors of the type shown in FIGS. 6–9 and described above.

Figure 9:
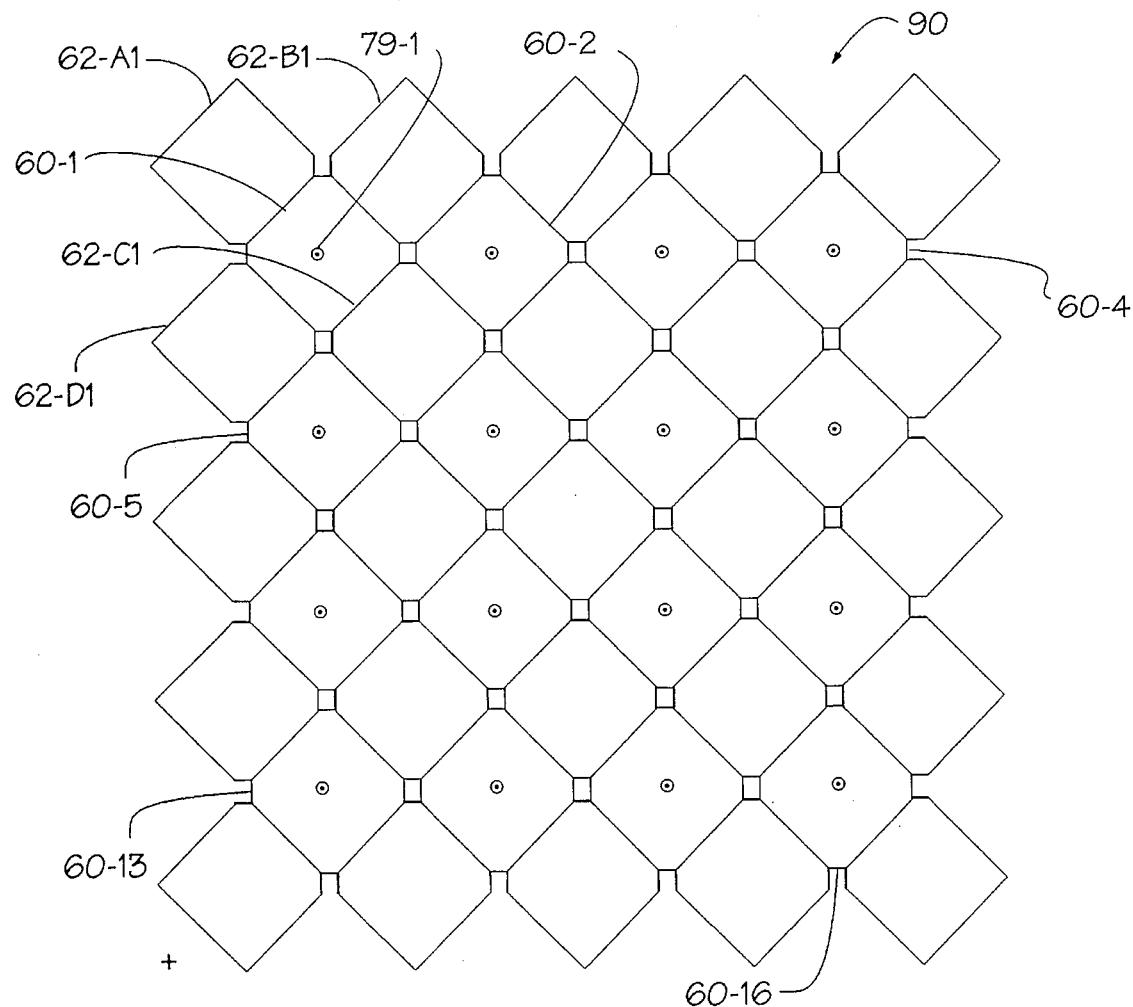
FIG. 9 is a fragmentary upper plan view of an array of sensors of the type shown in FIG. 6, showing an upper cover sheet thereof removed to reveal construction details of the sensor array.

FIG. 9 is a plan view of a 4×4 square array 90 of square shear sensors 60 of the type described above. Referring back to FIG. 6, it may be seen that each shear sensor 60 has a central conductive square-shaped pad 61 and 4 square-shaped peripheral conductive pads 62 labelled in a clockwise direction as 62-A, 62-B, 62-C and 62-D. A 4×4 array of spaced apart sensors 60 would thus require 64 peripheral conductive pads 62. However, by arranging sensors 60 into the close packed square tiling pattern shown in FIG. 9, all but the four peripheral conductor pads at the corners of the array contact more than one central conductive pad 61, thereby decreasing the number of peripheral conductive pads required for the array from 64 to 25. Thus, as shown in FIG. 9, upper left-hand corner peripheral conductor pad 62-A1 conducts only one central conductive pad, 60-1, but peripheral conductive pad 63-B1 contacts two central conductive pads, 60-1 and 60-2. Also, peripheral conductive pad 62-C1 contacts three central conductive pads, 60-1, 60-2, and 60-6, while peripheral conductive pad 62-C1 contacts two central conductive pads, 60-1 and 60-5.

FIGS. 10 and 11 illustrate the upper surface of a flexible printed circuit 70 forming a support substrate for square sensor array 60. As shown in FIG. 11, flexible printed circuit 70 has on its upper surface 71 four separate conductive traces 72-1, 72-2, 72-3, and 72-4 that extend in serpentine paths across the surface of the flexible circuit from a ribbon cable connector 91 attached to one end of the flexible printed circuit. As shown in FIG. 10, insulating sheet 73 covers conductive traces 72, except for elongated rectangular-shaped perforations through the sheet, the perforations being vertically aligned with selected peripheral conductive pads 62. Thus, as shown in FIG. 10, each of the four peripheral conductive pads 62 adjacent each central conductive pad 61 overlies an opening 74 over a separate column trace 72. For example, referring to FIG. 11 in conjunction with FIG. 10, and viewing sensor 60-1 in the upper left-hand corner of sensor array 90, peripheral conductive pad 62-A1 overlies rectangular opening 73 through insulating superstrate sheet 73 covering flexible printed circuit 70. That opening in turn overlies column conductive trace 72-1. Electrical contact is made between conductive trace 72-1 and peripheral conductive pad 62-A by RTV 60C.

In an exactly analogous fashion, electrical connections are made between conductive trace 72-2 and peripheral conductive pad 62-D, trace 72-3 and peripheral conductive pad 62-B, and trace 72-4 and peripheral conductive pad 62-C.

FIG. 8, 9 and 12 illustrate the manner of making electrical connections to central conductive pads 61 of sensor array 90. As shown in FIG. 12, flexible printed circuit 70 has on its lower surface 77 16 separate conductive traces 78-1 through 78-16, arranged in rows extending across the board from ribbon cable connector 91 at one end of the flexible printed circuit. Each conductive trace 78 terminates in a separate via 79, located under the center of each central conductive pad 61. Electrical connection is made between each via 79 and a central conductive pad 61 as shown in FIG. 8 and described above.

Figure 13:
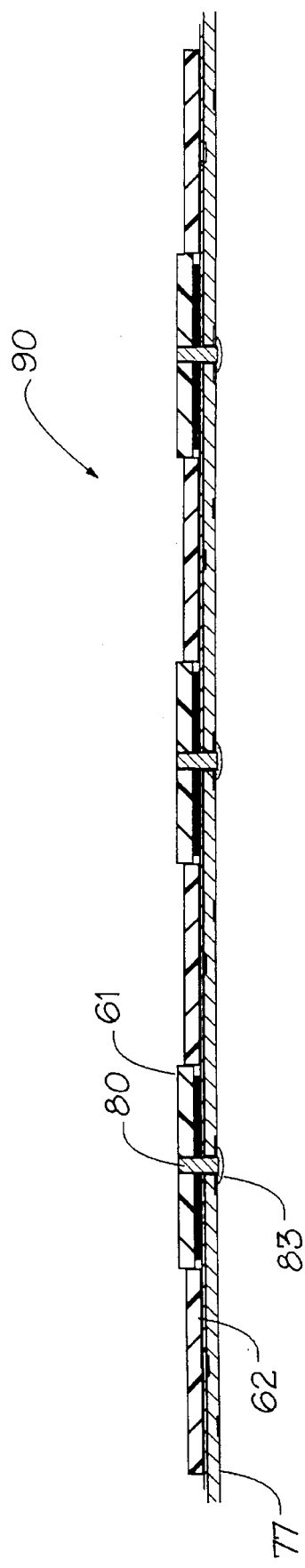
FIG. 13 is a transverse sectional view of the sensor array of FIG. 9.

FIG. 13 is a transverse sectional view of square shear sensor array 90.

Figure 14:
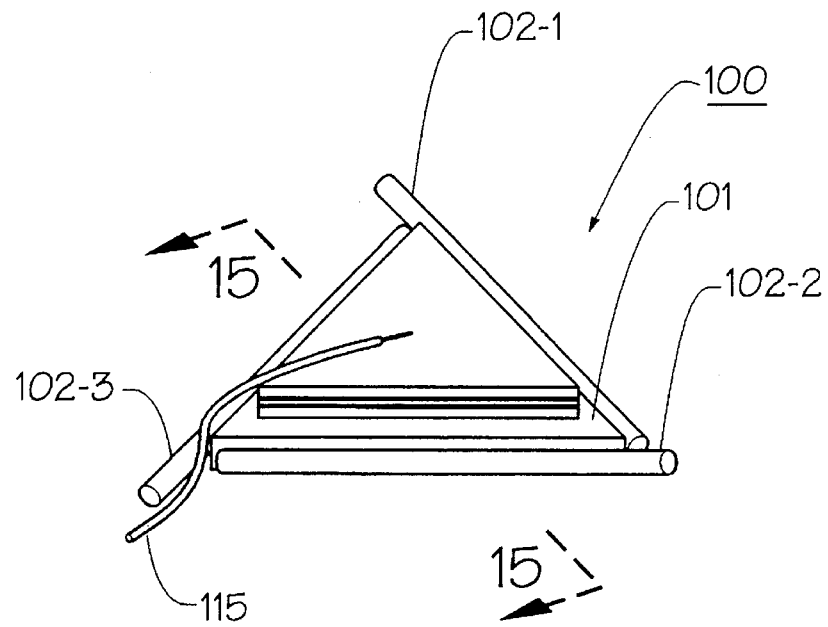
FIG. 14 is an upper plan view of a modification of the sensor of FIG. 6, which is capable of sensing normal forces.
Figure 15:
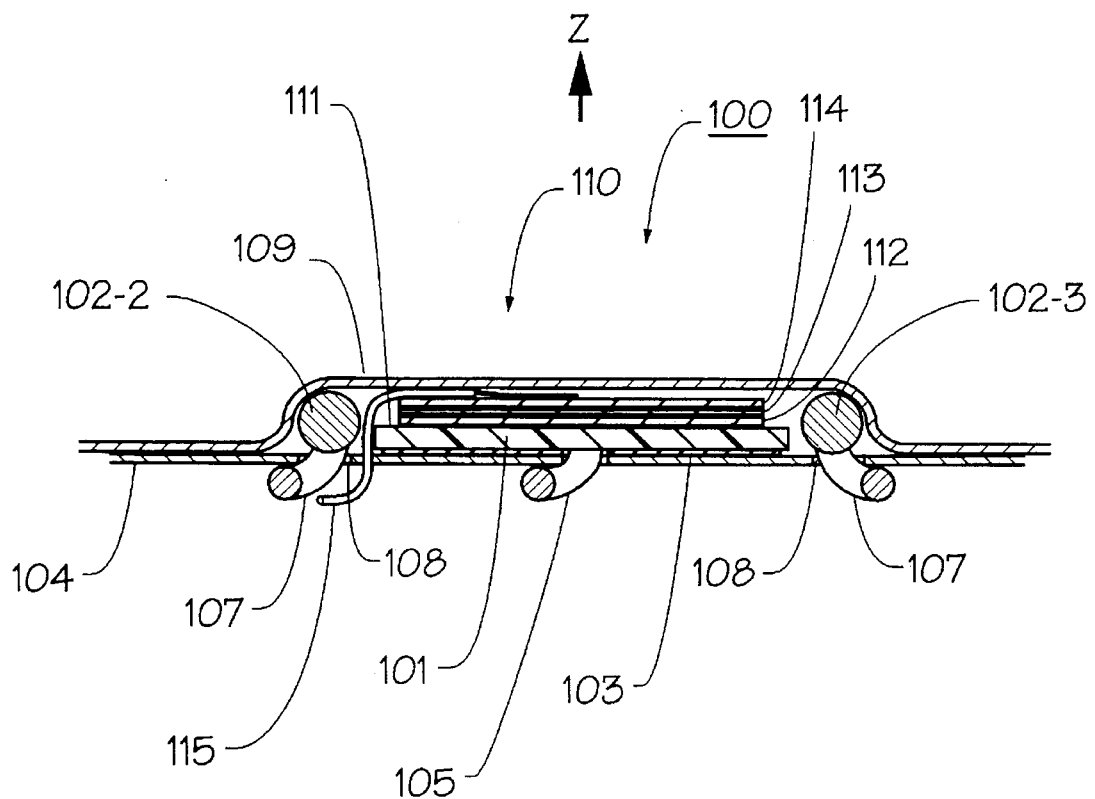
FIG. 15 is a transverse sectional view of the modified shear sensor of FIG. 14.

FIGS. 14 and 15 illustrate a modification of the triangular shear sensor 30 shown in FIGS. 1 and 2. Modified sensor 100 has shear sensor elements 101 through 109 substantially identical in structure and function to elements 31 through 39, respectively, of shear sensor 30 described above. Sensor 100 includes additional elements that provide means for measuring normal forces exerted on the sensor, i.e., forces perpendicular to the plane of the sensor, designated as force N in the -Z direction in FIG. 15. Thus, as shown in FIGS. 14 and 15, dual function sensor 100 includes a normal force sensor 110 located on the upper surface 111 of central conductive elastomeric pad 101. Normal force sensor 110 includes a lower flat electrode 112, perferably made of a thin, metallic fabric such as the Flectron™ copper/nickle coated polyester fabric described above. Also included in normal force sensor 110 is a resiliently deformable, partially conductive layer 113 that has an electrical resistance inversely proportional to normal forces or pressures exerted on the layer, a property which may be referred to as volume or bulk piezoresistivity. The present inventor has found that a suitable material for forming piezoesistive layer 113 is an ink composed of about 50% milled carbon black having a grain size of 2–5 microns, 30% unpolymerized liquid nitrile rubber, type BUNA N and 20% ABS plastic resin/hardener, or silicone rubber (e.g., Dow Corning RTV 732) and no hardener. Piezoresistive layer 112 is formed by mixing the aforementioned components thoroughly, applying the mixture to a thickness of about 0.004 in. on the upper surface of lower electrode 112, placing an upper electrode 114 substantially identical to lower electrode on top of the semi-liquid piezoresistive mixture, and allowing the mixture to air cure at room temperature.

The volume resistivity of normal force sensor 110 can be varied to a desired cured value by varying the amount of carbon black added to the liquid rubber, and monitoring the resistivity as those two components are being mixed together. The present inventor has found that a suitable range of volume resistivities for piezoresistive layer 113 is about 5 ohm-cm to 100,000 ohm-cm for measurement of normal forces in the approximate range of 0–5 psi, and 100–300,000 ohm-cm for measurement of forces in the approximate range of 5–30 psi.

Normal force sensor 110 includes means for making electrical connections to lower electrode 112 and upper electrode 114. In sensors 100 where the conductivity of central conductive pad 101 of the shear sensitive portion of the sensor is substantially larger than the nominal conductivity of piezoresistive layer 113, say by a factor of ten or more, common connecting wire 105 connected to lower sheet electrode 103 below the central conductive pad may optionally be used as one terminal of normal force sensor 110. The other terminal of normal force sensor 110 may consist of a connector wire 115, connected to upper flat electrode 114 by RTV 60C. As shown in FIG. 15, upper normal force electrode connector wire 115 is led out of sensor package 100 through a space between a pair of peripheral conductive cylinders 102.

Figure 16:
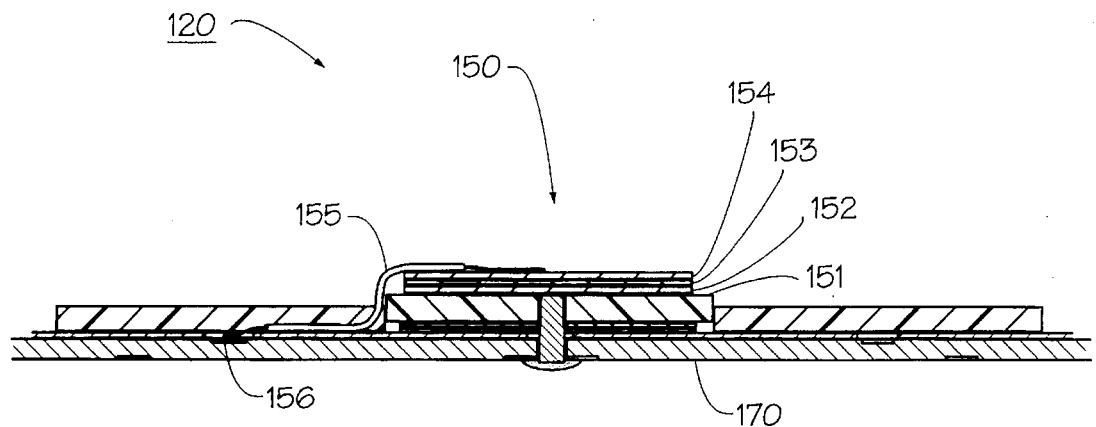
FIG. 16 is a first transverse sectional view of another embodiment of a combined shear/normal force sensor.
Figure 17:
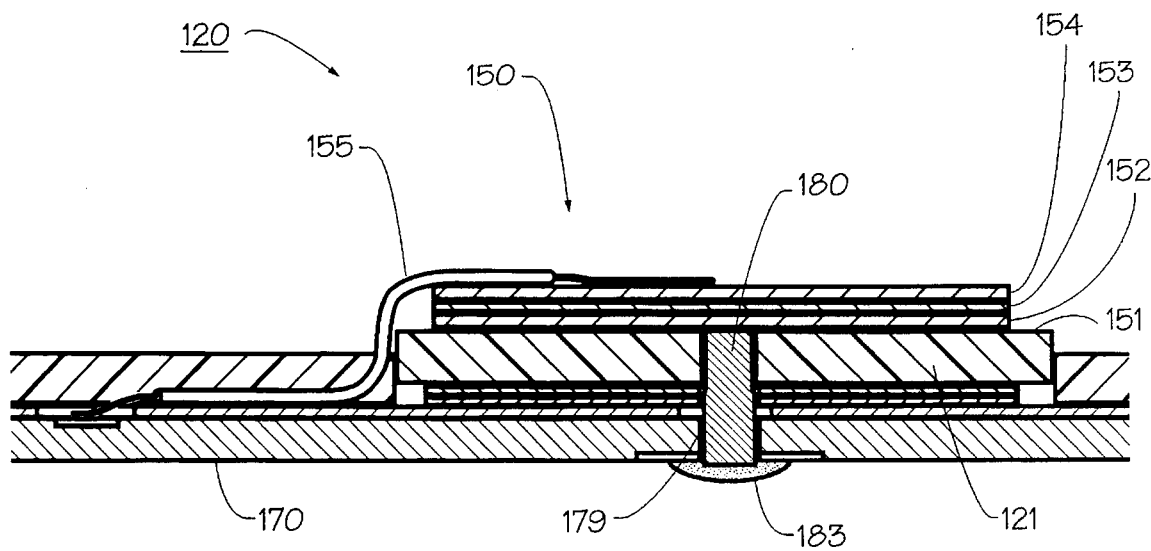
FIG. 17 is a second transverse sectional view of the sensor of FIG. 16, on a somewhat enlarged scale.

FIG. 16 and 17 illustrate a modification of the square shear sensor 60 shown in FIGS. 6–8. Modified, dual function shear sensor 120 has a normal force sensing capability provided by the addition of a normal force sensor 150 to the shear sensor 60 shown in FIGS. 6–8 and described above.

As shown in FIGS. 16 and 17, modified sensor 120 has shear sensor elements 121 through 124, and 130–143 substantially structurally and functionally to elements 61 through 64, and 70–83, respectively, of shear sensor 60 described above. In addition to the aforementioned shear sensor elements, as shown in FIGS. 16 and 17, dual function sensor 120 includes a normal force sensor 150 located on the upper surface 151 of central conductive elastomeric pad 121. Normal force sensor 150 includes a lower flat electrode 152, preferably made of thin metallic fabric, a piezoresistive layer 153, and an upper electrode 154. Except for having square rather than triangular plan-view shapes, the previously mentioned elements are identical in structure and function to the corresponding elements of normal force sensor 110 shown in FIG. 15 and described in detail above. Normal force sensor 150 includes an upper electrode connector wire 155 connected to upper electrode 154. As shown in FIG. 16, normal force sensor connector wire 155 of dual function sensor 120 is connected to a trace 156 on a flexible printed circuit substrate 170.

Figure 18:
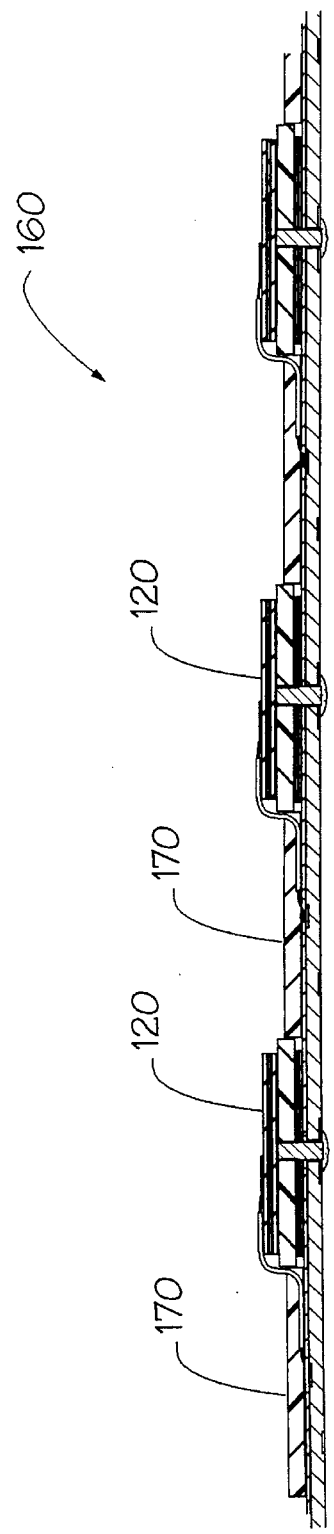
FIG. 18 is a side elevation view of an array of sensors of the type shown in FIG. 17.

FIG. 18 is a side elevation of a square array 160 of dual function sensors of the type shown in FIGS. 16 and 17 and described above.

Figure 19:
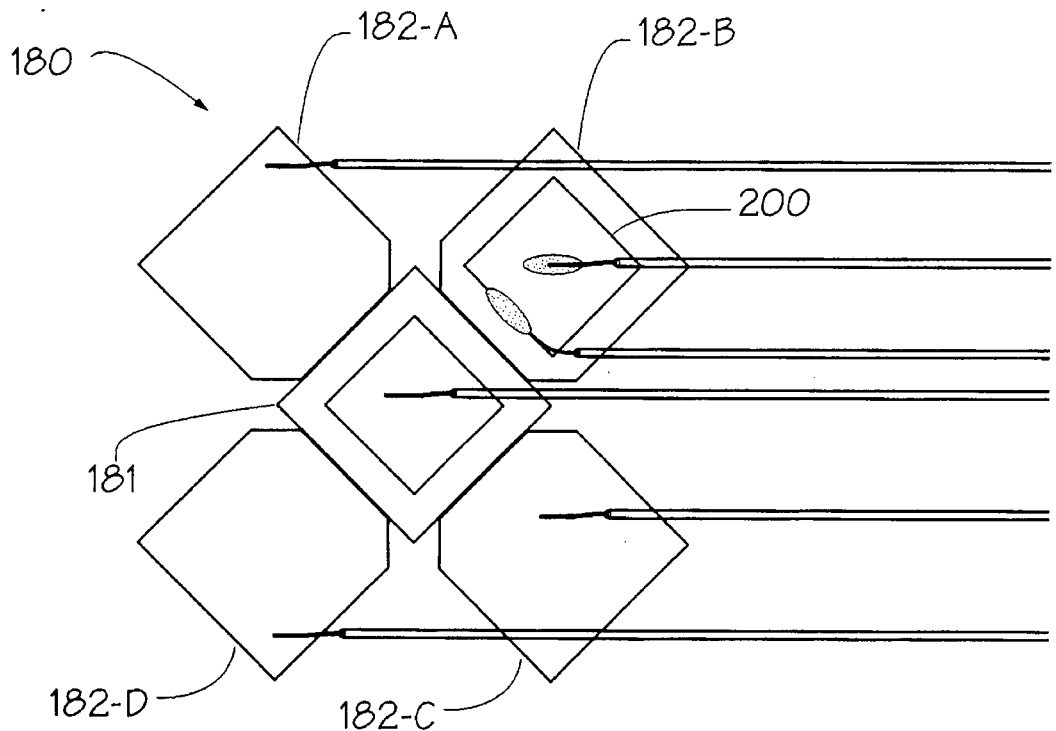
FIG. 19 is a plan view of another embodiment of a shear/normal force sensor according to the present invention.

FIG. 19 illustrates a modification of the dual function force sensor 120 shown in FIGS. 16 and 17 described above. In the modified dual function sensor 180, a square plan-view normal force sensor 200 substantially identical in structure and function to normal force sensor 150 shown in FIGS. 16 and 17 and described above is attached to the upper side of a peripheral conductive pad 182, rather than to central conductive pad 181. As shown in FIG. 19, one or more peripheral conductive pads, such as 182-B and 182-C shown in FIG. 19, may be modified to include a normal force sensor 200.

Figure 20:
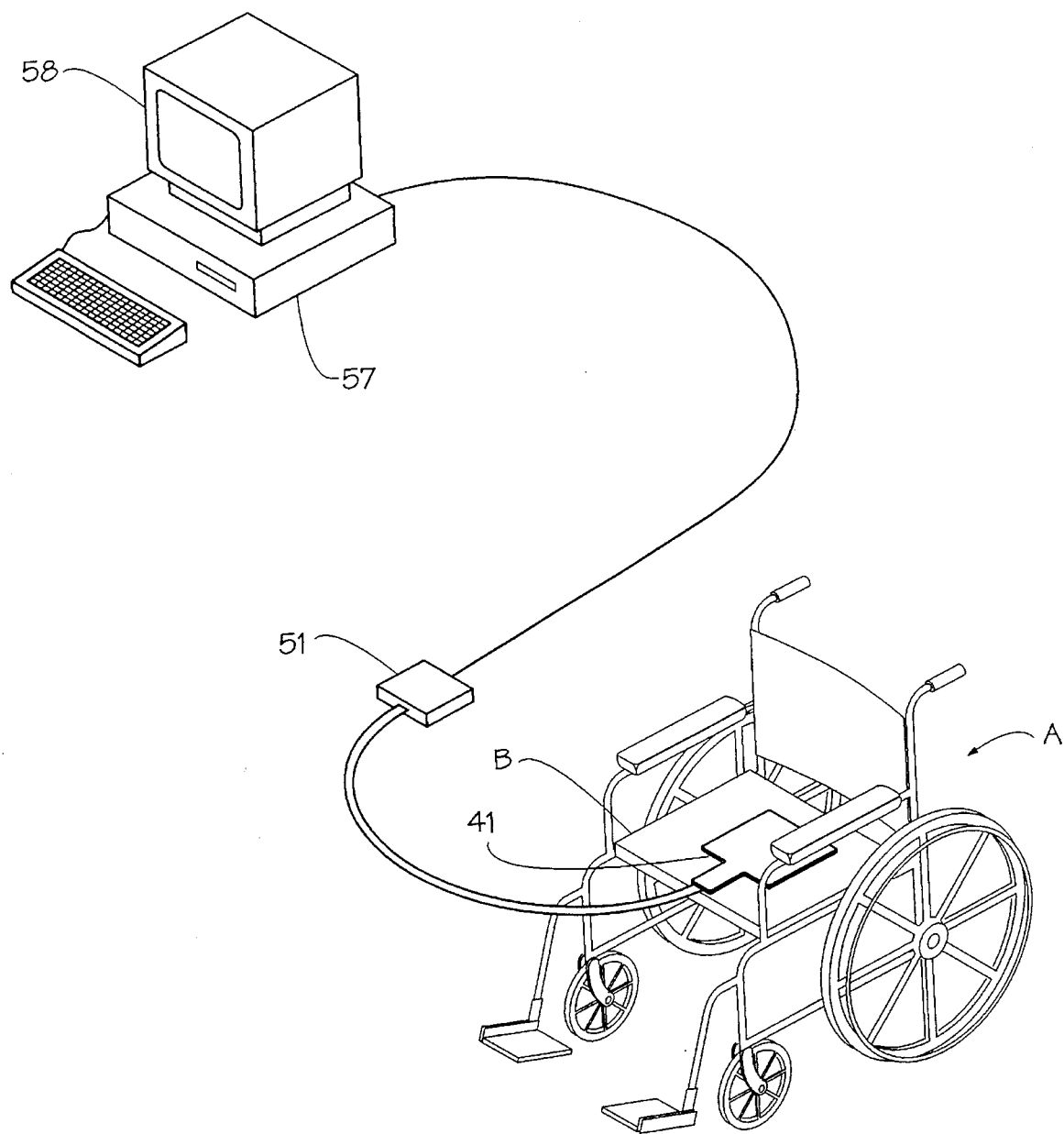
FIG. 20 is a perspective view of a force sensing array according to the present invention, showing the array placed on a wheel chair and interconnected with a computer and monitor.

FIG. 20 is a perspective view of a force sensing array according to the present invention, showing the array placed on a wheel chair pad and interconnected with a computer and monitor.

As shown in FIG. 20, a sensor array 41 is placed on the upper surface of the seat pad B of a wheel chair A, and interconnected via interface module and multiplexer 51 to a computer 57 and monitor 58. This arrangement is well suited to measuring shear forces exerted on the buttocks of a patient seated in the wheel chair, when the patient slides forward in the chair. Such measurements are valuable for monitoring shear forces exerted on patients with cerebral palsy, since a person afflicted with this ailment often experiences muscle spasms that cause the person to slide out of the wheel chair, causing shear forces to be exerted which can cause the formation of pressure ulcers, or aggravate already existing ulcers.

The configuration shown in FIG. 20 is primarily for use in diagnosing seating designs and configurations, and monitoring on a short term basis shear and normal pressures exerted on a patient's body. However, those skilled in the art will recognize that interface module 51 may be connected to circuitry which produces an audible or visible alarm when the magnitude and direction of shear or normal forces sensed by the present invention deviate from predetermined limit bands.

To locate the exact source of pressures and shear forces, it is sometimes helpful to be able to view and obtain an image of an area being sensed. The modified sensor shown in FIGS. 21 and 22 satisfies this need.

Figure 21:
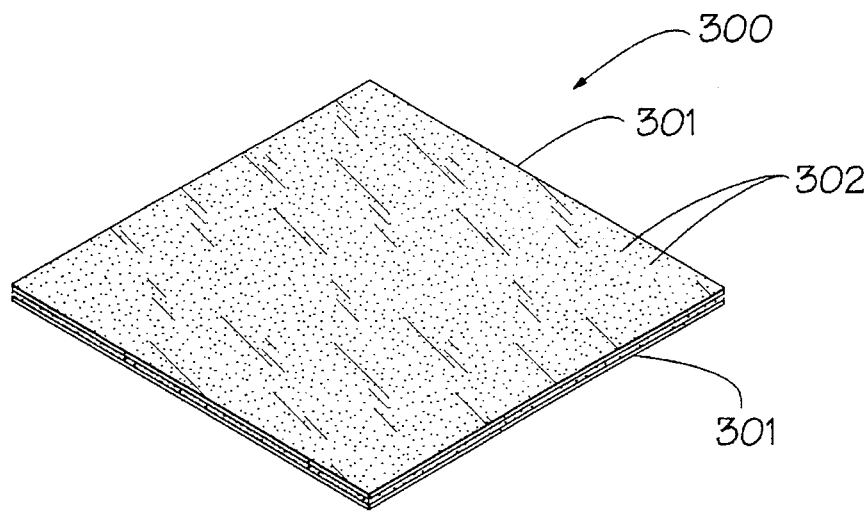
FIG. 21 is a perspective view of a transparent force sensor according to the present invention.
Figure 22:
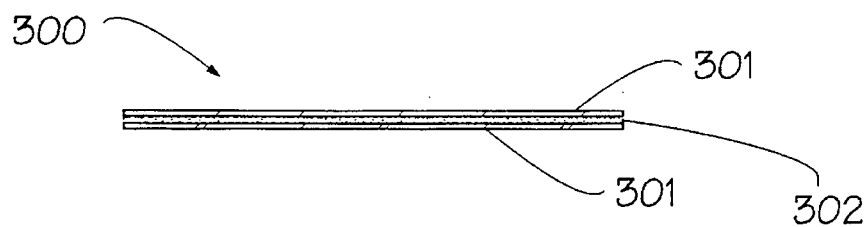
FIG. 22 is a side elevation view of the sensor of FIG. 21.

As shown in FIGS. 21 and 22, modified sensor 300 utilizes in substitution for Flectron sheets clear polyester upper and lower sheets 301 that are coated with a transparent conductive film, preferably indium tin oxide (ITO). One of the two sheets is lightly dusted with a semi-liquid piezoresistive material containing conductive grains of a material such as carbon black, suspended in a liquid polymer matrix, such as silicone rubber or neoprene. An air brush works well in applying the piezoresistive coating onto the conductive ITO film. The individual droplets 302 of uncured piezoresistive material, which are substantially opaque, must be far enough apart to allow optical transmission of an image through the sensor, but close enough to prevent the upper and lower polyester sheets from contacting one another. The present inventor has found that a nominal spacing of about 0.020 inch meets the aforementioned two requirements. After the droplets of piezoresistive material have been applied to a sheet 301, the other sheet is adhered to the droplet-coated sheet, and the droplets allowed to cure.

Another application for the shear force sensors according to the present invention and described above, is the use of the sensor to sense sideways force of a finger pressed against the sensor, using the magnitude and direction of sensed shear forces to control the motion of a cursor on a computer screen. The advantage of this system is that it can be made very thin and could be placed on the top of lap top or notebook type computers. In addition, the forces required to activate the sensor and cursor can be quite small and therefore be useable by handicapped people who have limited or week motion capabilities. A shear force sensor of this type may also be used to enter written characters into a computer by pressing a pen onto the sensor, and moving the pen to generate characters viewed on a computer monitor.

What is claimed is:

1. A force sensor for producing an electrical signal proportional to forces exerted on said sensor comprising;

a. a first type conductive member, b. at least one second type conductive member movable into resiliently deformable, electrically conductive contact with said first type conductive member, the area and electrical conductance of said contact being proportional to forces urging said first and second type conductive member together, said contact being characterised by a surface piezoresistivity inversely related to said forces and greater than the resistivity of said first conductive member, c. means for supporting said first and second type conductive members, and d. means for making external electrical contact to said first and second type conductive members.

2. The sensor of claim 1 wherein said first type conductive member is further defined as being a resilient conductive pad.

3. The sensor of claim 2 wherein said second type conductive member is further defined as being an elongated member in peripheral contact with said first conductive member.

4. The sensor of claim 3 wherein said second type conductive member is further defined as being contactable with a first side wall of said first type conductive member.

5. The sensor of claim 4 further including at least one additional second type conductive member contactable with an additional side wall of said first type conductive member.

6. A shear sensor for producing an electrical signal proportional to shear forces exerted thereon comprising;

a. a base having a generally flat upper surface, b. a conductive resilient pad on said flat upper surface, c. at least one peripheral conductive member adjacent a side wall of said conductive pad, said resilient pad and peripheral conductive member being resiliently contactable in response to relative motion therebetween caused by shear forces exerted on said sensor in a direction parallel to said base, the area and electrical conductance of said contact being proportional to said shear forces.

7. The shear sensor of claim 6 wherein said conductive pad is further defined as having a polygonal plan-view shape.

8. The shear sensor of claim 6 wherein said conductive pad is further defined as being made of a conductive elastomeric polymer.

9. The shear sensor of claim 8 wherein said conductive elastomeric polymer is further defined as being rubber containing solid particles of conductive material.

10. The shear sensor of claim 9 wherein said rubber is further defined as being selected from the group comprising silicone rubbers and nitrile rubbers.

11. The shear sensor of claim 9 wherein said solid particles are further defined as being carbon black.

12. The shear sensor of claim 7 wherein said sensor is further defined as including a plurality of peripheral conductive members, one each adjacent a separate side wall of said polygonally-shaped conductive pad.

13. The shear sensor of claim 12 wherein said peripheral conductors are each further defined as an elongated straight member having a resiliently deformable surface adjacent a side wall of said conductive pad.

14. The shear sensor of claim 12 wherein said peripheral conductor is further defined as an elongated flexible cylinder made of an elastomeric material.

15. The shear sensor of claim 14 wherein said flexible cylinder is further defined as having on the surface thereof an electrically conductive coating.

16. The shear sensor of claim 15 wherein said elastomeric material is further defined as being a silicone rubber.

17. The shear sensor of claim 15 wherein said conductive coating is further defined as containing conducting particles.

18. The shear sensor of claim 13 wherein said conductive pad is further defined as having a triangular plan-view shape.

19. The shear sensor of claim 18 wherein said plurality of peripheral conductors is further defined as three, one each adjacent a separate one of the three side walls of said conductive pad.

20. The shear sensor of claim 12 wherein said conductive pad is further defined as having a rectangular plan-view cross section.

21. The shear sensor of claim 20 wherein said peripheral conductors are each further defined as being a rectangular plan-view conductive elastomeric pad having a straight side wall adjacent a side wall of said central conductive pad.

22. A piezoresistive pressure sensor comprising;
 a. a first conductive electrode,
 b. a piezoresistive layer overlying said first electrode, and
 c. a second conductive electrode overlying said piezoresistive layer, at least one of said first and second electrodes being a uniformly metallized fabric sheet, said uniform metallization enabling said fabric sheet to drape.

23. The pressure sensor of claim 22 wherein said piezoresistive layer is further defined as a compressible nonconductive matrix filled with conducting particles.

24. The pressure sensor of claim 23 wherein said matrix is further defined as being an elastomeric polymer.

25. The pressure sensor of claim 24 wherein said conductive particles are further defined as being suspended within said elastomeric polymer.

26. The pressure sensor of claim 25 wherein said conductive particles are further defined as being carbon.

27. The pressure sensor of claim 26 wherein said carbon is further defined as being in the form of carbon black.

28. The pressure sensor of claim 26 wherein said carbon is further defined as being in the form of graphite.

29. The pressure sensor of claim 22 wherein said metallized fabric sheet is further defined as having a polymer substrate.

30. The pressure sensor of claim 29 wherein said polymer is further defined as being a polyester.

31. A shear sensor array for producing electrical signals proportional to shear forces exerted at various locations over an area in contact with said array, said array comprising;
 a. a thin substrate having first and second substantially parallel surfaces,
 b. a plurality of shear force sensors mounted to said substrate, each of said shear force sensors comprising,
  i. a central, square plan-view, thin conductive elastomeric pad mounted parallel to a surface of said substrate,
  ii. a plurality of square plan-view peripheral conductive elastomeric pads mounted parallel to a surface of said substrate, each of said peripheral pads having a straight side wall adjacent a side wall of said central conductive pad, said side walls being resiliently deformable in response to shear forces to make more or less electrically conductive contact therebetween, said central and peripheral conductive pads arranged in a close-packed tiling pattern whereby some of said peripheral conductive pads contact more than one central conductive pad, and
 c. means for making electrically conductive connections to each of said central conductive pads and each of said peripheral conductive pads.

32. The shear sensor array of claim 31 wherein said substrate is further defined as being a thin flexible, electrically nonconductive material.

33. The shear sensor array of claim 32 wherein said means for making electrically conductive connections to said central and peripheral conductive pads is further defined as conductive printed circuit traces on at least one surface of said substrate.

34. The shear sensor array of claim 33 further including a normal force sensor attached to the surface of at least one of said central conductive pads or peripheral conductive pads.

35. The shear sensor array of claim 34 wherein said normal force sensor is further defined as comprising;
 a. a piezoresistive layer in contact with a surface of said central conductive pad or said peripheral conductive pad,
 b. a flexible planar electrode overlying and in contact with said piezoresistive layer, and
 c. means for making electrical connection to said overlying planar electrode, whereby the electrical resistance of said piezoresistive layer may be monitored by applying an electrical signal between said overlying electrode and said conductive pad.

36. The sensor array of claim 35 further including a second, underlying flexible planar electrode located between said conductive pad and said piezoresistive layer, said underlying electrode constituting an equipotential plane.

* * * * *